United States Patent [19]

Lanno et al.

[11] 4,275,821

[45] Jun. 30, 1981

[54] DRIVE SYSTEM AND FLUID DISPENSER UNIT UTILIZING SAME

[76] Inventors: Joseph P. Lanno, 60 Woodcliff Dr., Waltham, Mass. 02154; Fred M. Finnemore, 76 Park St., North Reading, Mass. 01864

[21] Appl. No.: 75,951

[22] Filed: Sep. 17, 1979

[51] Int. Cl.$^3$ ............................................. B67D 5/08
[52] U.S. Cl. ..................................... 222/61; 74/411; 239/274; 222/63
[58] Field of Search ...................... 74/130, 141.5, 142, 74/411, 109, 470; 222/70, 52, 61, 63, 394, 402.1, 509; 239/274

[56] References Cited

U.S. PATENT DOCUMENTS

| | | | |
|---|---|---|---|
| 1,760,902 | 6/1930 | Grattan | 74/142 |
| 3,589,563 | 6/1971 | Carragan | 222/70 |
| 3,608,784 | 9/1971 | Brown | 222/509 |
| 3,656,509 | 4/1972 | Yasu | 222/70 |
| 4,030,638 | 6/1977 | Lanno | 239/274 |

Primary Examiner—H. Grant Skaggs

[57] ABSTRACT

A mechanical drive system for providing a maximum limit on the magnitude of unidirectional output motion in response to reciprocating input motion, including: an output member moveable in a first direction; a unidirectional drive for driving said output member in said first direction; limiter chain for limiting the motion of the unidirectional drive in the first direction to define a limit position; and an override drive mechanism responsive to the reciprocating input motion occurring in one direction to move the unidirectional drive to a rest position and to the reciprocating input motion occurring in the opposite direction to move the unidirectional drive in the first direction from the rest position no further than the limit position, irrespective of the extent of the reciprocating input motion to the override drive mechanism; and a periodically actuated fluid dispenser unit utilizing such a drive mechanism.

13 Claims, 4 Drawing Figures

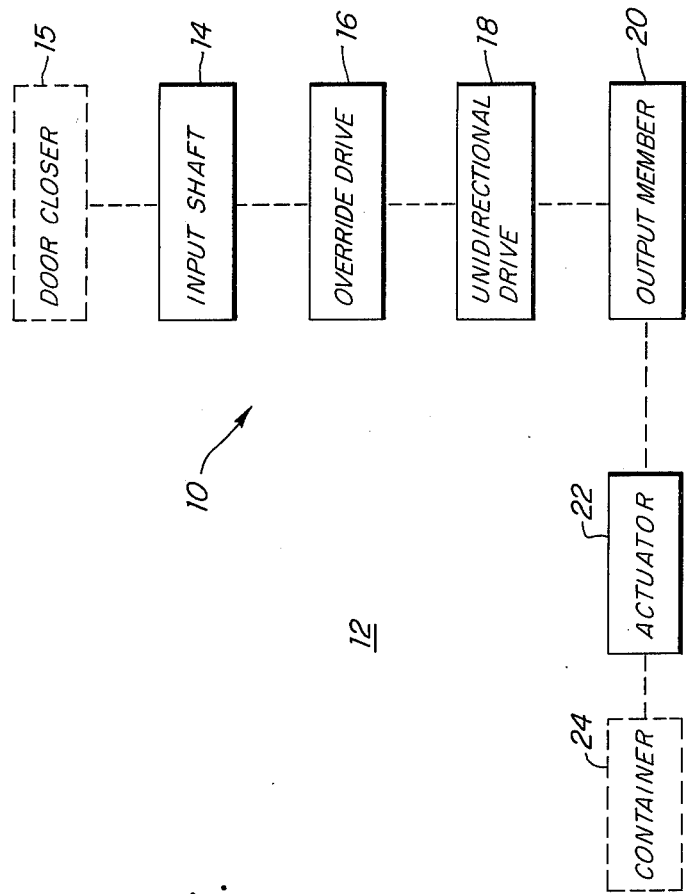
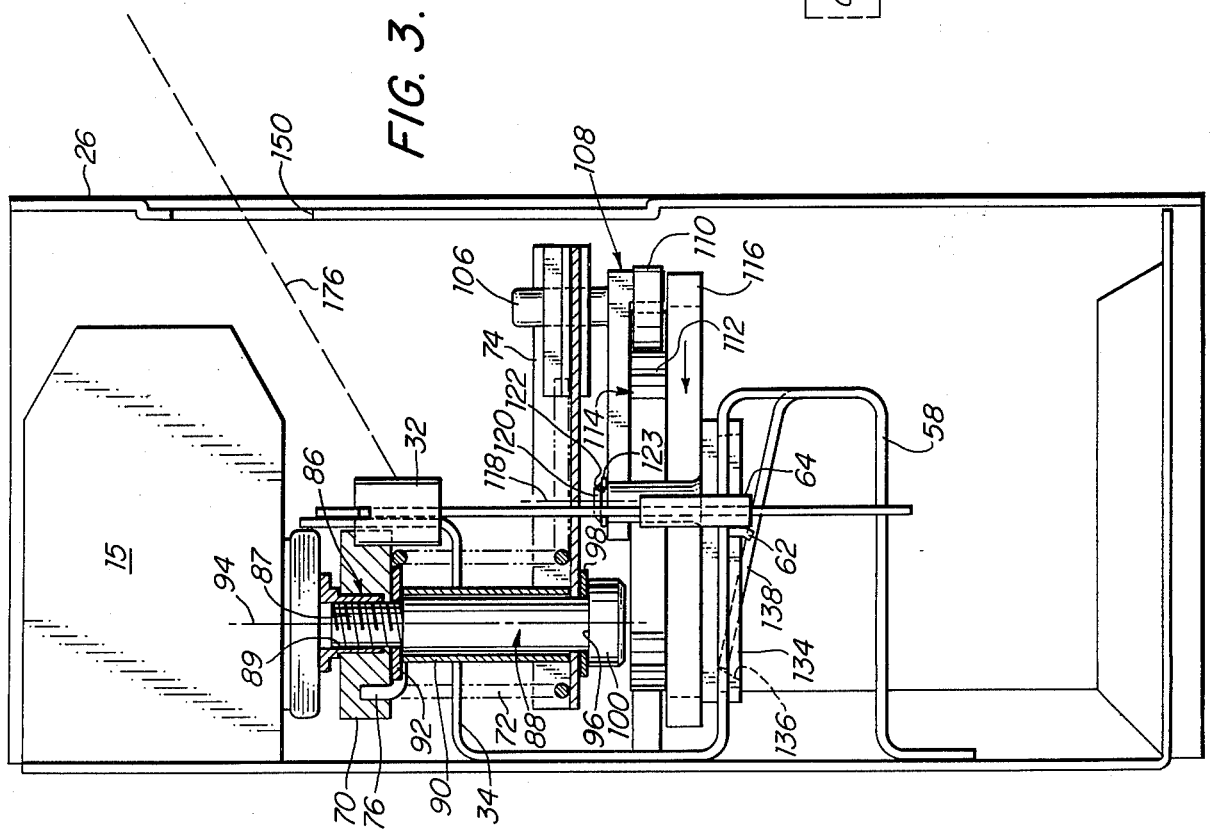

4,275,821

DRIVE SYSTEM AND FLUID DISPENSER UNIT UTILIZING SAME

FIELD OF INVENTION

This invention relates to a drive system which provides a maximum limit on the magnitude of unidirectional output motion in response to reciprocating input motion, and to a periodically activated fluid dispenser unit utilizing such a drive mechanism.

BACKGROUND OF INVENTION

Conventional mechanisms for automatically dispensing fluids such as deodorants, disinfectants, insecticides and the like, use a number of different mechanisms. For example, in one device a synchronized motor is used to periodically operate an aerosol dispenser; in another, the movement generated by the withdrawal of a towel from a towel dispenser drives a fan to move air over a block of deodorant. In some arrangements door motion is used to operate mechanical drives that move air across a deodorant, while in others more sophisticated mechanical linkages are used, such as toggles and bellows, to actuate valves and aerosol devices. Those devices that are driven by the motion of a door were typically restricted to a fixed dispensing pattern; for example they dispense the fluid each time the door is opened and/or closed, which often results in too frequent or too infrequent dispensing of the fluid. Overdispensing was undesirable, especially in the case where the fluid included pesticides, insecticides, and other harmful substances which were undesirable and could be injurious to the persons working in the area. More recently, a fluid dispenser which could be operated by door motion was disclosed, U.S. Pat. No. 4,030,638, using a cam member driven by an output shaft, typically an extension of a door closer. A cam follower actuator responsive to the cam member operates a fluid dispenser container such as an aerosol can to dispense the fluid at least once during each rotation of the cam member. In that design the cam member could be driven for only a portion of a full rotation upon each operation of the door closer unit and the cam could have one or a number of functional surfaces to operate the follower actuator to provide some flexibility in selecting the number of times dispensation would occur for determining the ratio of dispensations to door openings and closings. This approach too suffered some shortcomings; for example, it is difficult to easily, predictably adjust the ratio of dispensation to door closings, and the mechanism was relatively complex and expensive.

SUMMARY OF INVENTION

It is therefore an object of this invention to provide an improved, simplified, and less expensive drive system and a fluid dispenser unit utilizing such a drive sytem which are easier and less expensive to manufacture.

It is a further object of this invention to provide such a drive system which provides a maximum limit on the magnitude of unidirectional output motion in response to reciprocating input motion.

It is a futher object of this invention to provide such a drive system in which the limit on unidirectional output motion is easily adjustable.

It is a further object of this invention to provide such a drive system in which the relationship of door openings and/or closings and dispensations is more easily predictable and set.

The invention results from the realization that a unidirectional output motion suitable for driving a dispenser system can be obtained from a reciprocating input motion, such as provided by a door closer mechanism, by utlizing a unidirectional drive and an override drive mechanism which responds to the reciprocating input motion in one direction to move the unidirectional drive to a rest position and to reciprocating input motion in the other opposite direction to move the unidirectional drive from the rest position no farther than the limit position, irrespective of the extent of the reciprocating input motion to the override drive mechanism.

The invention features a mechanical drive system for providing a maximum limit on the magnitude of unidirectional output motion in response to reciprocating input motion. There is an output member moveable in a first direction and a unidirectional drive for driving said output member in said first direction. Limiter means limit the motion of the unidirectional drive in the first direction to define a limit position. An override drive mechanism responsive to the reciprocating input motion occurring in one direction drives the unidirectional drive to a rest position and, responsive to the reciprocating motion occurring in the other opposite direction, drives the unidirectional drive in the first direction from the rest position no farther than the limit position, irrespective of the extent of the reciprocating input motion to the override drive mechanism.

In one embodiment the drive mechanism is used in a fluid dispenser unit which periodically dispenses fluid from a container in response to a reciprocating input motion. The drive system may include an actuator member driven by the output member to operate a fluid dispensing container or other device. The output member may be a rotatable cam. The unidirectional drive may include a ratchet member fixed to the output member and a ratchet drive engageable with the ratchet member by means of a pawl. The override drive mechanism may include a spring and first drive member for receiving the reciprocating input motion and having means for engaging one end of the spring means. A second drive member engages the other end of the spring means and the ratchet drive. The actuator means may include a pivot member and a spring member for biasing the pivot member to a first state.

DISCLOSURE OF PREFERRED EMBODIMENT

Other objects, features and advantages will occur from the following description of a preferred embodiment and the accompanying drawings, in which:

FIG. 1 is a block diagram of a drive mechanism in a fluid dispensing unit according to this invention;

FIG. 3 is a side elevational view of the drive system in the dispenser unit of FIG. 2 with the fluid dispenser container removed for clarity.

Figure 2:
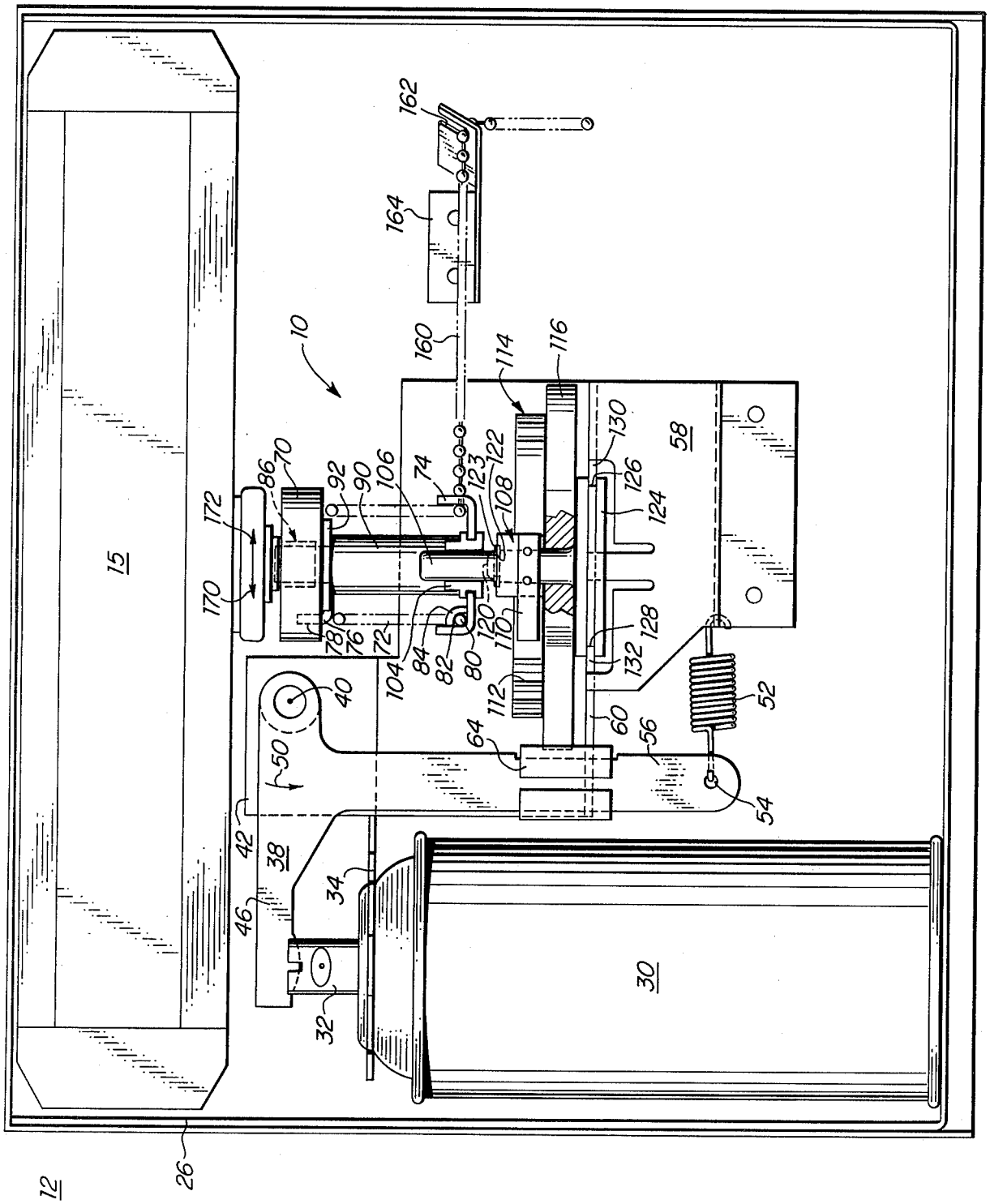
FIG. 2 is a front elevational view of a specific embodiment of the drive system in a dispenser unit according to this invention.

The invention may be accomplished using a drive block engaged with an input shaft such as from a door closer. A spring engages with the drive block and with an arm that carries a ratchet pawl. When the input shaft is rotated, it rotates the drive block which through the spring rotates the drive arm and ratchet pawl. The motion of the arm is limited by a chain or other link which is fixed at one end, for example, to the housing. Motion of the input shaft in that direction tending to move the arm beyond the defined limit is abosrbed by the spring after the arm has reached its limit. The ratchet pawl engages a ratchet gear, which is fixed to a cam. Each time the door is opened and closed the input shaft rotates in one direction to move the arm back to rest position, and in the other direction to move the arm toward the limit positon. As the arm with the ratchet pawl moves toward the limit position it drives the ratchet gear and cam. The cam has one or more surfaces which operate an actuator. For example, the cam may have a recess that allows a spring-biased bell crank to operate the valve of an aerosol dispenser can. The number of recesses in the cam surface determines the number of times per cam revolution that the aerosol valve will be operated. The extent of the motion between the rest position and the limit position sets the degree of rotation of the ratchet gear and cam for each opening and closing of the door. A second pawl may be used to prevent the ratchet gear from rotating in the opposite direction when the ratchet pawl is moved toward the rest position.

Generally, as shown in FIG. 1, a drive mechanism 10 utilized in a dispenser unit 12 according to this invention includes an input shaft 14 which derives a reciprocating input motion from a door closer 15, for example. The input shaft operates an override drive 16 which provides a fixed maximum amount of drive motion to unidirectional drive 18, irrespective of the full magnitude of the motion provided by input shaft 14. The unidirectional motion is imparted through output member 20, which operates some device, for example actuator 22, that periodically operates an aerosol valve on a container 24. The valve on container 24 is preferably a metered valve which delivers only a measured amount of fluid each time it is actuated to prevent excessive discharge if the mechanism malfunctions in the actuated condition.

In one embodiment, dispenser unit 12 may include a housing 26 which accommodates a conventional door closer 15, such as a spring loaded rack and pinion type, and an aerosol container 30 which contains the desired deodorant, pesticide, or the like. Container 30 includes an aerosol valve 32 and is held in place by a bracket 34, FIG. 4, mounted on housing 26.

Figure 4:
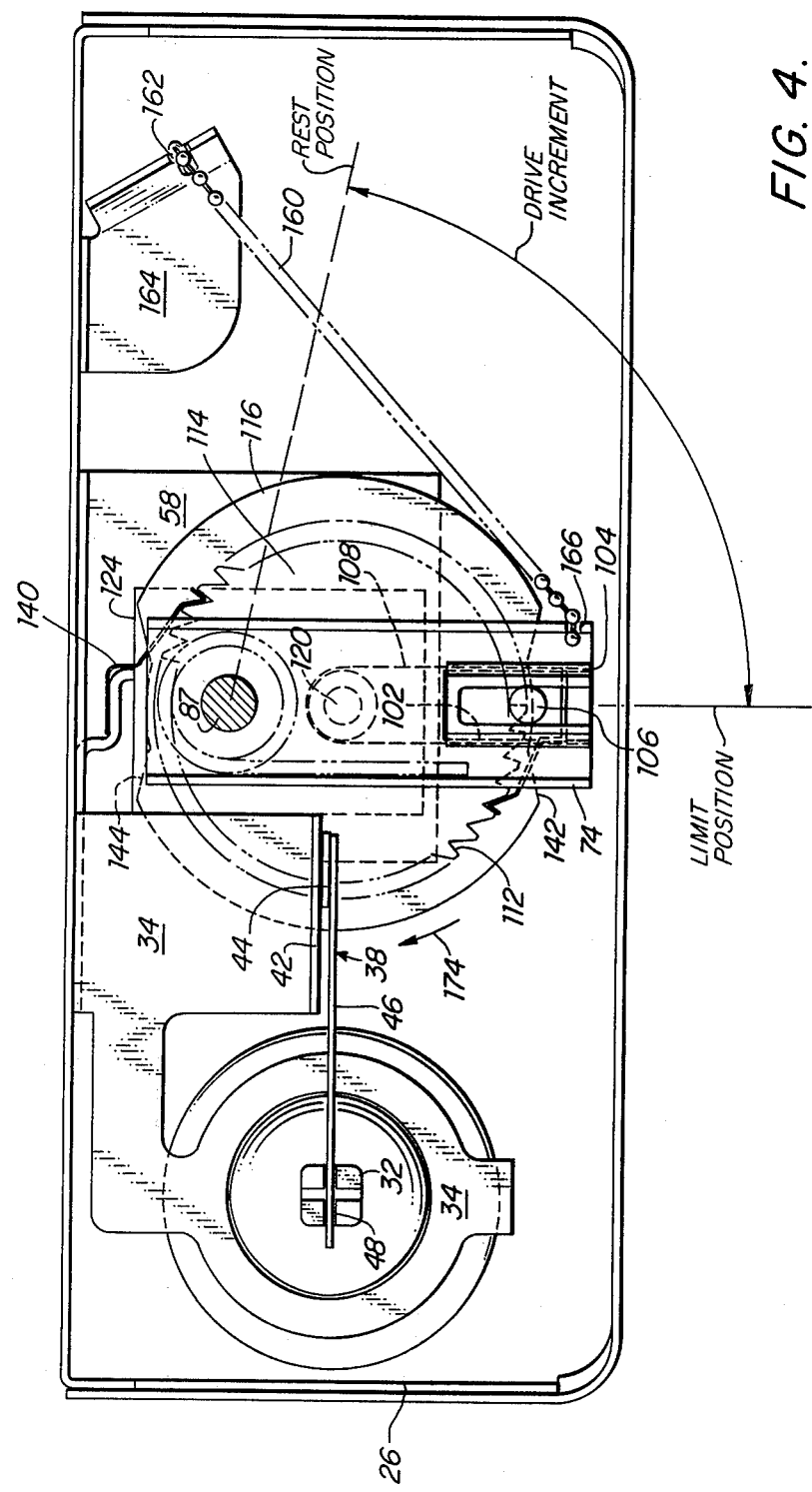
FIG. 4 is a plan view similar to FIGS. 2 and 3.

An actuator such as bell crank 38, FIG. 2, is pivotally connected at axis 40 to upstanding tab 42 of bracket 34 with a Teflon or other self-lubricating washer 44, FIG. 4, between them. The upper arm 46 of bell crank 38 engages with slot 48 of valve 32 and is constantly biased, to actuate valve 32 by moving it downwardly, arrow 50, by spring 52 which is attached in hole 54 in the lower arm 56 of bell crank 38. Spring 52 is attached to main bracket 58, which is also mounted on housing 26 and has an extension 60 that provides a side bearing 62, FIG. 3, that engages with self-lubricating sleeve 64 on the lower arm 56 of bell crank 38.

The drive system 10 uses an override drive mechanism that includes a drive collar 70, spring 72, and drive plate 74. The upper end 76 of spring 72 is received in a hole 78 in drive collar 70, while the lower end 80 is received in the recess 82 formed by piece 84, stamped from drive plate 74. Drive collar 70 with end 76 of spring 72 is fixed to rotate with shaft 86 of door closer 15 by means of shoulder bolt 88, whose threaded portion 87 engages with a similarly threaded portion 89 internally provided on shaft 86. Sleeve 90 and washer 92 are sized to permit rotation of driver plate 74 about axis 94 on shoulder 96 of shoulder bolt 88. A washer 98 supports driver plate 74 on head 100 of shoulder bolt 88. Driver plate 74 includes a slot 102, FIG. 4, in which is slidably engaged a self-lubricating bushing 104, FIG. 2, that engages upstanding pin 106, FIG. 3, of ratchet arm 108. Ratchet arm 108 carries pawl 110, FIG. 2, which engages with teeth 112, FIG. 3, on ratchet gear 114. Ratchet gear 114 is fixed to cam 116 so that they rotate together about their central axis 118 on pin 120, FIG. 3, which contains a recess 122 for receiving an E ring 123. Pin 120 is integral with base 124, which has recesses 126 and 128 that engage with lips 130, 132, on main bracket 58. Base 124 also has a recess 134 with an inclined rear wall 136 that receives a locking section 138 stamped from bracket 58. A stationary pawl 140, FIG. 4, supported from housing 26, engages with teeth 112 on ratchet gear 114 to ensure that the gear does not slip backwards as driver plate 74 is moved to the rest position. Cam 116 includes two actuator surfaces 142, 144, which when brought in juxtaposition to sleeve 64 allow spring 52 to rotate bell crank 38 in the direction of arrow 50 and operate aerosol valve 32 to dispense fluid through a hole 150, FIG. 3, in the front of housing 126. The motion of driver plate 74 is limited by some limiting device, for example bead chain 160, which is anchored in slot 162 of a reference mounting 164 fixed to housing 26. The other end of bead chain 160 is placed in slot 166, FIG. 4, in driver plate 74. The amount of rotation imparted to cam 116 by each reciprocating operation of shaft 86 is limited by means of chain 160. The drive increment between the rest position and limit position of driver plate 74, FIG. 4, can be shortened by moving the limit position line closer to the rest position line by simply lifting bead chain 160 out of slot 162, pulling it to the right and reinserting it in slot 162. Conversely, the drive increment can be increased by loosening bead chain 160 to move the limit position farther away from the rest position.

In operation, as the door to which housing 26 is affixed is opened and closed, door closer 15 provides reciprocating input motion at its shaft 86, as indicated by arrows 170 and 172. When shaft 86 is rotating in the direction of arrow 172 it causes drive collar 70 to rotate spring 72 in the same direction and move driver plate 74 to the rest position as shown in FIG. 4. When input shaft 86 rotates in the opposite direction as indicated by arrow 170, it causes collar 70 to drive spring 72 and driver plate 74 in the direction toward the limit position, FIG. 4.

When the limit position is reached, additional input motion from shaft 86 in the direction of arrow 170 is accommodated by spring 72 without further rotation of driver plate 74. Each time driver plate 74 is so driven from the rest position to the limit position, its pawl 110 engages teeth 112 and drives ratchet gear 114 along with cam 116 in the clockwise direction 174, FIG. 4. This motion periodically results in one of cam surfaces 142, 144 releasing the restriction on sleeve 64 so that the force of spring 52 can rotate bell crank 38 and actuate valve 32 to provide a spray 176 out opening 150 in housing 26. Motion in the direction 172 moves driver plate 74 with pawl 110 back toward the rest position, but does not draw cam 114 back in the same direction. In fact, stationary pawl 140 is used to ensure that no such backward motion of ratchet gear 114 and cam 116 is permitted.

The override mechanism in conjunction with limiting chain 160 thus provides a means for positive continuous adjustment of the drive increment irrespective of the magnitude of the input motion of shaft 86, and the number of actuations of valve 32 per revolution of gear 114 and cam 116 is determined by the number of operative camming surfaces 142, 144. Thus the number of dispensations of spray 176 per average door closing can be closely controlled.

Other embodiments will occur to those skilled in the art and are within the following claims:

What is claimed is:

1. A mechanical drive system for providing a maximum limit on the magnitude of unidirectional output motion in response to reciprocating input motion comprising:
    an output member moveable in a first direction;
    a unidirectional drive for driving said output member in said first direction;
    limiter means for limiting the motion of said unidirectional drive in said first direction to define a limit position; and
    an override drive mechanism responsive to said reciprocating input motion occurring in one direction to drive said unidirectional drive to a rest position and to said reciprocating input motion ocurring in the opposite direction to drive said unidirectional drive in said first direction from said rest postion no farther than said limit position and absorbing input motion beyond said limit position.

2. The mechanical drive system of claim 1 further including actuator means driven by said output member.

3. The mechanical drive system of claim 1 in which said output member is rotatable.

4. The mechanical drive system of claim 3 in which said output member is a cam.

5. The mechanical drive system of claim 1 in which said unidirectional drive includes a ratchet member and a ratchet drive for driving said ratchet member.

6. The mechanical drive system of claim 5 in which said ratchet member is fixed to said output member.

7. The mechanical drive system of claim 5 in which said ratchet drive inlcudes a pawl for engaging said ratchet member.

8. The mechanical drive system of claim 1 in which said override drive mechanism includes spring means, a first drive member for receiving said reciprocating input motion and having means for engaging one end of said spring means; and a second drive member for engaging the other end of said spring means and said ratchet drive.

9. The mechanical drive system of claim 1 in which said actuator means includes a pivot member and a spring member biasing said pivot member to a first state.

10. A fluid dispenser unit for periodically dispensing fluid in a container in response to a reciprocating input motion comprising:
    actuator means for operating a fluid dispensing container to dispense fluid;
    an output member moveable in a first direction for periodically operating said actuator means;
    a unidirectional drive for driving said output member in said first direction;
    limiter means for limiting the motion of said unidirectional drive in said first direction to define a limit position; and
    an override drive mechanism responsive to said reciprocating input motion occurring in one direction to drive said unidirectional drive to a rest position and to said reciprocating input motion occurring in the opposite direction to drive said unidirectional drive in said first direction from said rest position no farther than said limit position and absorbing input motion beyond said limit position.

11. A fluid dispenser unit for periodically dispensing fluid in a container in response to a reciprocating input motion comprising:
    actuator means for operating a fluid dispensing container to dispense fluid;
    a cam member rotatable in a first direction for periodically operating said actuator means at least once each revolution;
    a unidirectional drive for driving said cam member in said first direction;
    limiter means for limiting the motion of said unidirectional drive in said first direction to define a limit position; and
    an override drive mechanism responsive to said reciprocating input motion occurring in one direction to drive said unidirectional drive to a first position and to said reciprocating input motion occurring in the opposite direction to drive said unidirectional drive in said first direction from said rest position no farther than said limit position and absorbing input motion beyond said limit position; said override drive mechansim including:
    spring means, a first drive member for receiving said reciprocating input motion and having means for engaging one end of said spring means; and
    a second drive member for engaging the other end of said spring means and said unidirectional drive.

12. A mechanical drive system for providing a maximum limit on the magnitude of unidirectional output motion in response to reciprocating input motion comprising:
    an output member moveable in a first direction;
    a unidirectional drive for driving said output member in said first direction;
    limiter means for limiting the motion of said unidirectional drive in said first direction to define a limit position; and
    an override drive mechanism responsive to said reciprocating input motion occurring in one direction to drive said unidirectional drive to a rest position and to said reciprocating input motion occurring in the opposite direction to drive said unidirectional drive in said first direction from said rest position no farther than said limit position and absorbing input motion beyond said limit position; said override drive mechanism including spring means, a first drive member for receiving said reciprocating input motion and having means for engaging one end of said spring means; and a second drive member for engaging the other end of said spring means and said unidirectional drive.

13. A fluid dispenser unit for periodically dispensing fluid in a container in response to a reciprocating input motion comprising:
    actuator means for operating a fluid dispensing container to dispense fluid;
    an output member moveable in a first direction for periodically operating said actuator means;
    a unidirectional drive for driving said output member in said first direction;

limiter means for limiting the motion of said unidirectional drive in said first direction to define a limit position; and an override drive mechanism responsive to said reciprocating input motion occurring in one direction to drive said unidirectional drive to a rest position and to said reciprocating input motion occurring in the opposite direction to drive said unidirectional drive in said first direction from said rest position no farther than said limit position and absorbing input motion beyond said limit position; said override drive mechanism including spring means, a first drive member for receiving said reciprocating input motion and having means for engaging one end of said spring means; and a second drive member for engaging the other end of said spring means and said unidirectional drive.

* * * * *